United States Patent [19]
Fujiwara

[11] Patent Number: 6,083,958
[45] Date of Patent: Jul. 4, 2000

[54] ANTI-HIV COMPOSITION CONTAINING IMIDAZOLE DERIVATIVE

[75] Inventor: Tamio Fujiwara, Nishinomiya, Japan

[73] Assignee: Shionogi & Co., Ltd., Japan

[21] Appl. No.: 09/155,655

[22] PCT Filed: Mar. 14, 1997

[86] PCT No.: PCT/JP97/00812

§ 371 Date: Oct. 2, 1998

§ 102(e) Date: Oct. 2, 1998

[87] PCT Pub. No.: WO97/37657

PCT Pub. Date: Oct. 16, 1997

[30] Foreign Application Priority Data

Apr. 4, 1996 [JP] Japan ................................. 8-082563
Apr. 8, 1996 [JP] Japan ................................. 8-085132

[51] Int. Cl.[7] ..................... A61K 31/415; A61K 31/445; A61K 31/47

[52] U.S. Cl. ..................... 514/311; 514/316; 514/397; 514/398

[58] Field of Search ...................... 514/397, 398, 514/311, 316

[56] References Cited

U.S. PATENT DOCUMENTS 5,910,506   6/1999   Sugimoto et al. ...................... 514/397

OTHER PUBLICATIONS

Eric DeClerck, Journal of Medicinal Chemistry, vol. 38 (14), pp. 2491–2517, Jul. 1995.

Decker et al., Research Articles, Metabolism of Amprenavir in Liver Microsomes, pp. 803–807, Apr. 16, 1998.

*Primary Examiner*—Alan L. Rotman
*Attorney, Agent, or Firm*—Wenderoth, Lind & Ponack, L.L.P.

[57] ABSTRACT

An anti-HIV composition comprising 2-carbamoyloxymethyl-5-(3,5-dichlorophenylthio)-4-isopropyl-1-(pyridin-4-yl)methyl-1H-imidazole or the pharmaceutical acceptable salt thereof and other one or more anti-HIV compounds is provided.

8 Claims, 2 Drawing Sheets

ANTI-HIV COMPOSITION CONTAINING IMIDAZOLE DERIVATIVE

TECHNICAL FIELD

The present invention relates to pharmaceutical compositions comprising two or more anti-HIV compounds.

BACKGROUND ART

AIDS (Acquired immunodeficiency syndrome) has been sweeping worldwide as an intractable disease caused by HIV (human immunodeficiency virus). The research and development of the therapeutic agents are also performed globally, however, have not given satisfaction yet. At present, anti-HIV compositions which have been used or tested clinically are exemplified by nucleoside derivatives such as azidodeoxythymidine (AZT), dideoxyinosine (ddI), dideoxycytidine (ddC), dideoxydidehydrothymidine (d4T), 3'-thiacytidine (3TC), and the like as main therapeutic agents.

But all of these agents have serious side effects such as pancreatitis, anemia, leukopenia, neutropenia, emesis, aphagia, gastric disorder, anthema, insomnia, illusion, myospasm, dyspnea, dysuria, renal insufficiency, hypacusis, and the like. The agents have many problems such as the emergence of drug resistant viruses by the prolonged administration and followed by reduction of efficacy of agents, and the like.

In order to reduce these problems, at present, the treatment with multiple anti-HIV compositions have been generally adopted.

Under these situations, it has been reported that administration of multiple anti-HIV compounds show synergy. The examples of the synergy are combination of 3TC with non-nucleoside anti-HIV compounds such as {[(benzoxazol-2-yl)methyl]amino}-5-alkyl-6-alkyl-2-(1H)-pyridinone and the like disclosed in JP-A 7-508997, and similar combination of 3TC with 11-cyclopropyl-5,11-dihydro-4-methyl-6H-dipyrido[3,3-b;21,31-e][1,4]diazepin-6-one disclosed in JP-A 7-508998.

Problems such as serious side effects of anti-HIV compounds, the emergency of resistant viruses, and the like are pointed out. New combination of anti-HIV compounds which show synergy, that is, compositions comprising the compounds as an active ingredient have been desired.

DISCLOSURE OF INVENTION

The present inventors found that administration of 2-carbamoyloxymethyl-5-(3,5-dichlorophenylthio)-4-iropropyl-1-(pyridin-4-yl) methyl-1H-imidazole (referred to as a CDIMI hereinafter) or the pharmaceutical acceptable salt thereof in combination with other one or more anti-HIV compounds gives synergy by raising anti-HIV activity of each other.

Accordingly, one of the objects of the present invention is to provide an anti-HIV composition comprising CDIMI or the pharmaceutical acceptable salt thereof and other one or more anti-HIV compounds. The present invention also provides a method for treating or preventing of AIDS which comprises administering CDIMI or the pharmaceutical acceptable salt thereof simultaneously or continuously with other one or more anti-HIV compounds.

Another object of the present invention is to provide a use of CDIMI or the pharmaceutical acceptable salt thereof and anti-HIV compounds, for the manufacture of a medicament for treating or preventing of AIDS. The present invention further relates to a method for inhibiting propagation of HIV by contacting HIV virus to CDIMI or the pharmaceutical acceptable salt thereof in combination with other one or more anti-HIV compounds. The present invention relates to combination of CDIMI or the pharmaceutical acceptable salt thereof with other one ore more anti-HIV compounds.

CDIMI of the present invention is described in WO 96/10019 and the synthesis and the anti-HIV activity of the compound have been disclosed in the specification.

BEST MODE FOR CARRYING OUT THE INVENTION

Figure 1:
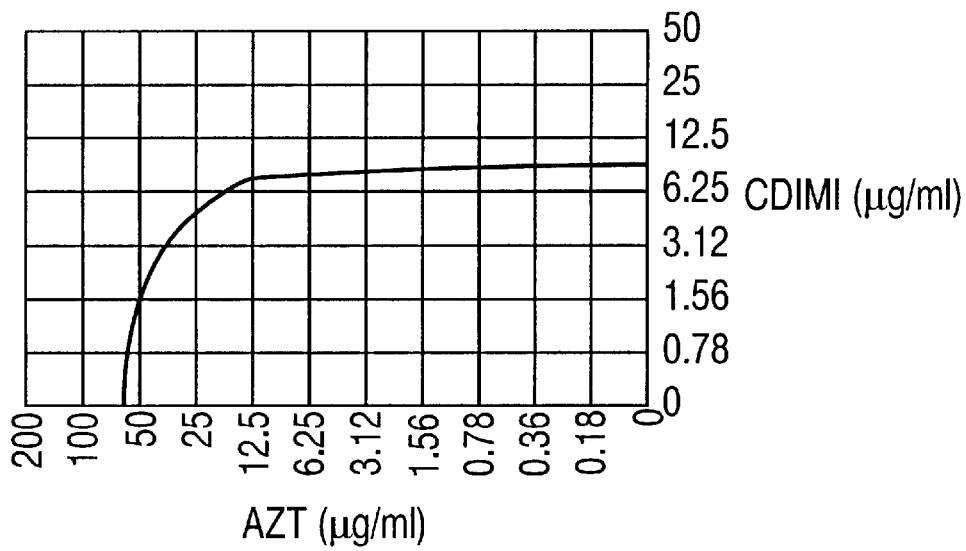
FIG. 1 shows correlation a concentration of an anti-HIV compound and a toxicity ($CC_{50}$) CEM cells.

In the present specification, pharmaceutical acceptable salts of CDIMI include, for example, salts with inorganic acids such as hydrochloric acid, sulfuric acid, nitric acid, phosphoric acid, hydrofluoric acid, hydrobromic acid, and the like, salts with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, and the like, and salts with alkali metals or alkali earth metals such as sodium, potassium, calcium, and the like.

The term "anti-HIV compound" of the present invention means any compounds having anti-HIV activity without particular limitation, for example, anti-virus compounds having anti-HIV activity such as a nucleoside reverse transcriptase inhibitor, a non-nucleoside reverse transcriptase inhibitor, an HIV protease inhibitor, a DNA polymerase inhibitor, and the like.

In the embodiment, a nucleoside reverse transcriptase inhibitor includes AZT, ddI, ddC, d4T, 3TC, and the like, a non-nucleoside reverse transcriptase inhibitor includes the compounds described in WO 96/10019, for example, 3-(5-(3,5-dichlophenylthio)-4-isopropyl-1-(pyridin-4-ylmethyl)-1H-imidazol-2-ylpropan-1-ol or 2-[5-(3,5-dichlorophenylthio)-1-ethyl-4-isopropyl- 1H-imidazol-2-yl] ethanol, and the like, an HIV protease inhibitor includes saquinavir, indinavir, ritonavir, nelfinavir, VX-478, and the like. The other medicaments having anti-HIV activity include, for example, foscarnet, a therapeutic agent of cytomegalovirus retinitis having DNA polymerase inhibition activity and reverse transcriptase inhibition activity, and the like. Particularly, AZT, ddI, ddC, 3TC, saquinavir, or foscarnet is preferred because of a high synergy of anti-HIV activity in combination with CDIMI. More particularly, AZT, ddI, ddC, saquinavir, or foscarnet is preferred, the most particularly, AZT, ddC or saquinavir is preferred. AZT and ddC which significantly inhibit the emergency of drug resistant viruses are most preferred.

An anti-HIV composition of the present invention can provide an effective treatment for AIDS because it shows synergy as compared to the administration of each anti-HIV compound and the like as a single agent. Specifically, because an anti-HIV composition of the present invention shows synergy of anti-HIV activity as shown in the following experiment, a less administration dose than that for a single agent of each anti-HIV compound gives enough anti-HIV activity, resulting in the reduction of side effects such as toxicity, and the like. Administration of the composition of the present invention which contains an equal amount of each anti-HIV compound to a dose for its single agent effectively inhibits the emergency of drug resistant viruses and obviously brings about potent and effective treatment.

Accordingly, an anti-HIV composition of the present invention is an effective pharmaceutical composition as a medicament for treating or preventing of AIDS.

The present invention is characterized by synergistic effect of CDIMI in combination with other one or more anti-HIV compounds. Accordingly, each active ingredient may be administered simultaneously as a composition. Continuous administration of each active ingredient at intervals of time that synergy is maintained gives the same effect.

When administering an anti-HIV composition of the present invention, it can safely be administered orally or parenterally. For oral administration, it may be administered as conventional formulations such as tablets, granules, powder, capsules, pilulae, liquid solutions, syrup, buccals, sublingual tablets, and the like. For parenteral administration, it can preferably be administered into any formulations, for example, injections such as intramuscular injection and the like, suppository, endermism, inhalations, and the like, in particular, oral administration is preferred.

The pharmaceutical composition of the present invention can be prepared by mixing an effective amount of active ingredients, if necessary, with medicinal additives suitable for a final administration formulation such as carriers, binders, wetting agents, disintegrating agents, lubricants, diluents, and the like. For example, injections may be prepared by sterilization with suitable carriers.

In the embodiment, carriers include lactose, sucrose, glucose, starch, calcium carbonate, crystalline cellulose, and the like, binders include methylcellulose, carboxymethylcellulose, hydroxypropylcellulose, gelatin, polyvinylpyrolidone, and the like, disintegrating agents include carboxymethylcellulose, sodium carboxymethylcellulose, starch, sodium alginate, powdered agar, sodium lauryl sulfate, and the like, and lubricants include talc, magnesium stearate, macrogol, and the like. Bases of suppositories include cocoa butter, macrogol, methylcellulose, and the like. In preparing liquid preparations or emulsion or suspension injection, conventional solubilizing agents, emulsifiers, stabilizing agents, preservatives, isotonizing agents, and the like may be added, and additionally. For oral administration, sweetening agents, flavoring agents, and the like may be added.

As an active ingredient of an anti-HIV composition of the present invention, CDIMI may be combined with one or more of other anti-HIV compounds.

In the case of administering CDIMI or other anti-HIV active compounds as a single agent, the administration dose for each active ingredient is usually 0.05 mg–3000 mg/day, preferably 0.1 mg–1000 mg/day, parenterally 0.01 mg–1000 mg/day, preferably 0.05 mg–500 mg/day.

In the case of administering an anti-HIV composition of the present invention, the dose of each active ingredient in the formulation should be determined in consideration of the patients' age and body-weight, the condition of diseases, the administration route, and the like. However, the amount of each active ingredient in the composition may be 0.1–1 times as the above administration dose of the each anti-HIV compound as a single agent. Accordingly, in the case of administering CDIMI and other anti-HIV compounds together as an anti-HIV composition of the present invention, the dose of each active ingredient may be 0.005 mg–3000 mg/day, preferably 0.01 mg–1000 mg/day for oral administration, 0.001 mg–1000 mg/day, preferably 0.005 mg–500 mg/day for parenteral administration. It can be administered in one to several times divisions per day.

EXAMPLE

Examples and Experiments of the present invention are provided to further illustrate in detail the present invention and are not to be construed as limiting the scope.

Experiment 1
Synergy of Anti-HIV Activity

Human T cell line Molt-4 cells persistently infected with HIV-1 (IIIB strain clone 2) were cultured in RPMI-1640 medium supplemented with 10% fetal calf serum, and the supernatant was filtered and stored at −80° C. after the virus titer was determined.

Two-fold dilution of CDIMI concentration from 10 ng/ml to 0.157 ng/ml and 0 ng/ml, and two-fold dilution of AZT concentration from 100 ng/ml to 0.4 ng/ml and 0 ng/ml were prepared. The combination of these two drugs was conducted by the checker board method using 96-well microplates. Fifty $\mu$l of the above medium containing $10^5$ cells/ml of MT-4 was added to each well of 96-well microplates, and 50 $\mu$l of AZT two-fold diluted by the same medium was added to each well. After 4 hours, 50 $\mu$l of the culture supernatant of the above HIV-1 IIIB strain clone 2 was added, at the same time 50 $\mu$l of CDIMI in two-fold dilution was also added, followed by incubation in 5% $CO_2$ incubator at 37° C. for 5 days.

Virus titers in the culture supernatant were calculated by taking viral reverse transcriptase activity as an index determined by the following method:

To 100 $\mu$l of a reaction mixture containing 50 mM Tris-HCl, pH 8.3, 150 mM KCl, 10 mM $MgCl_2$, 0.1% Nonidet P-40, 10 mM dithiothreitol, 5 $\mu$g/l poly(A), 5 $\mu$g/ml $(dT)_{12-18}$, and 1 $\mu$Ci [$^3$H]dTTP was added 10 $\mu$l of the culture supernatant, and incubated at 37° C. for 3 hours. The reaction mixture was chilled on ice and transferred by a cell harvester to a DEAE-Filtermat. The filter was washed with 5% $Na_2HPO_4 \cdot 12H_2O$ and $H_2O$, and the radioactivity incorporated in DNA was measured by an LKB Beta Plate scintillation counter to determine viral reverse transcriptase activity.

Three assays were conducted and the mean value of reverse transcriptase inhibition rate (%) was calculated by being compared to the enzymatic activity in the absence of CDIMI and AZT. The result is shown in Table 1.

TABLE 1

| | | \multicolumn{10}{c}{A Z T (ng/ml)} | | | | | | | | | |
|---|---|---|---|---|---|---|---|---|---|---|---|
| | | 0 | 0.4 | 0.8 | 1.6 | 3.13 | 6.25 | 12.5 | 25 | 50 | 100 |
| CDIMI (ng/ml) | 10 | 99.72 | 99.69 | 99.69 | 99.7 | 99.69 | 99.7 | 99.66 | 99.67 | 99.62 | 99.64 |
| | 5 | 99.63 | 99.67 | 99.65 | 99.61 | 99.63 | 99.61 | 99.62 | 99.64 | 99.63 | 99.63 |
| | 2.5 | 99.62 | 99.64 | 99.61 | 99.62 | 99.64 | 99.61 | 99.64 | 99.63 | 99.63 | 99.65 |
| | 1.25 | 99.07 | 99.57 | 99.6 | 99.6 | 99.56 | 99.59 | 99.62 | 99.64 | 99.61 | 99.65 |
| | 0.625 | 77.94 | 99.33 | 99.55 | 99.6 | 99.55 | 99.6 | 99.62 | 99.63 | 99.63 | 99.65 |
| | 0.313 | 3.02 | 96.72 | 98.33 | 99.44 | 99.4 | 99.54 | 99.61 | 99.65 | 99.67 | 99.68 |
| | 0.157 | −14.4 | 79.15 | 92.19 | 98.89 | 99.03 | 99.44 | 99.41 | 99.63 | 99.68 | 99.67 |
| | 0 | 0 | −7.82 | 43.43 | 77 | 96.3 | 98.6 | 99.33 | 99.56 | 99.64 | 99.66 |

On the assumption that the inhibition of the two anti-HIV compounds was additive, virus growth inhibition rate was calculated on all combinations of concentrations according to the formula (I)

$$Z = X + Y(1-X) \quad (I)$$

wherein Z means an additive inhibition rate, X is an inhibition rate of CDIMI and Y is an inhibition rate of the other anti-HIV compound. For example, when CDIMI was 5 ng/ml and AZT was 0.8 ng/ml, X is 99.63% when CDIMI is 5 ng/ml and AZT is 0 ng/ml in Table 1, and Y is 43.43% when CDIMI is 0 ng/ml and AZT is 0.8 ng/ml in Table 1. Then the additive inhibition rate Z is calculated to be 99.79% according to the formula (I).

Next, a difference between the measured values in Table 1 and a calculated additive inhibition rate as the above was calculated. The result is shown in Table 2, and the 99% confidential limit value is shown in Table 3.

When the measured value is greater than the additive inhibition rate, namely, the value is more than 0 in Table 3, it is judged as having synergy. Synergy volume is designated as total sum of values more than 0 in Table 3.

According to the same method, data analysis was conducted on the experiment results using ddI, ddC, saquinavir, and foscarnet instead of AZT.

Addition to cells of saquinavir and foscarnet was done at the same time as that of CDIMI when the virus was infected. For the combination with ddC, ddI and saquinavir, the CDIMI concentration was ranged from 5 ng/ml to 0.08 ng/ml in two-fold dilution and 0 ng/ml, and the concentrations of ddC, ddI, saquinavir, and foscarnet were ranged from 500 ng/ml to 2 ng/ml in two-fold dilution and 0 ng/ml.

The result of the analysis is shown below. Tables 4–6 show the results of ddI, Tables 7–9 show the results of ddC, Tables 10–12 show the results of saquinavir, and Tables 13–15 show the results of foscarnet.

TABLE 2

| | | \multicolumn{10}{c}{A Z T (ng/ml)} | | | | | | | | | |
|---|---|---|---|---|---|---|---|---|---|---|---|
| | | 0 | 0.4 | 0.8 | 1.57 | 3.13 | 6.25 | 12.5 | 25 | 50 | 100 |
| CDIMI (ng/ml) | 10 | 0 | −0.01 | −0.15 | −0.24 | −0.3 | −0.3 | −0.34 | −0.33 | −0.38 | −0.36 |
| | 5 | 0 | 0.07 | −0.14 | −0.3 | −0.36 | −0.38 | −0.38 | −0.36 | −0.37 | −0.37 |
| | 2.5 | 0 | 0.05 | −0.18 | −0.29 | −0.35 | −0.38 | −0.36 | −0.37 | −0.37 | −0.35 |
| | 1.25 | 0 | 0.57 | 0.13 | −0.19 | −0.41 | −0.4 | −0.37 | −0.36 | −0.39 | −0.35 |
| | 0.625 | 0 | 23.12 | 12.03 | 4.67 | 0.37 | −0.09 | −0.23 | −0.27 | −0.29 | 0.27 |
| | 0.312 | 0 | 101.28 | 53.19 | 21.75 | 2.99 | 0.9 | 0.26 | 0.08 | 0.02 | 0.01 |
| | 0.157 | 0 | 102.5 | 56.91 | 25.2 | 3.26 | 1.04 | 0.18 | 0.13 | 0.09 | 0.06 |
| | 0 | 0 | 0 | 0 | 0 | 0 | 0 | 0 | 0 | 0 | 0 |

TABLE 3

| | | \multicolumn{10}{c}{A Z T (ng/ml)} | | | | | | | | | |
|---|---|---|---|---|---|---|---|---|---|---|---|
| | | 0 | 0.4 | 0.8 | 1.57 | 3.13 | 6.25 | 12.5 | 25 | 50 | 100 |
| CDIMI (ng/ml) | 10 | 0 | 0 | −0.099 | −0.214 | −0.274 | −0.249 | −0.289 | −0.304 | −0.329 | −0.36 |
| | 5 | 0 | 0.0443 | −0.089 | −0.274 | −0.334 | −0.303 | −0.354 | −0.283 | −0.293 | −0.293 |
| | 2.5 | 0 | 0.0243 | −0.129 | −0.213 | −0.247 | −0.303 | −0.283 | −0.242 | −0.319 | −0.273 |
| | 1.25 | 0 | 0.5186 | 0.0529 | −0.139 | −0.281 | −0.349 | −0.319 | −0.309 | −0.313 | −0.299 |
| | 0.625 | 0 | 23.069 | 11.927 | 4.5929 | 0.2672 | −0.013 | −0.179 | −0.167 | −0.213 | −0.219 |
| | 0.312 | 0 | 100.61 | 52.65 | 21.699 | 2.7587 | 0.8229 | 0.2343 | 0.0286 | 0 | 0 |
| | 0.157 | 0 | 101.91 | 54.417 | 24.917 | 3.1572 | 0.8858 | 0.0515 | 0.0786 | 0.0386 | 0.0086 |
| | 0 | 0 | 0 | 0 | 0 | 0 | 0 | 0 | 0 | 0 | 0 |

TABLE 4

|  |  | ddI (ng/ml) | | | | | | | | | |
|---|---|---|---|---|---|---|---|---|---|---|---|
|  |  | 0 | 2 | 4 | 8 | 16 | 31.25 | 62.5 | 125 | 250 | 500 |
| CDIMI (ng/ml) | 5 | 99.01 | 99.05 | 99 | 99.11 | 99.13 | 99.16 | 99.17 | 99.08 | 99.1 | 99.15 |
|  | 2.5 | 99.13 | 99.02 | 99.01 | 98.98 | 99.12 | 99.05 | 99.06 | 98.98 | 98.96 | 98.91 |
|  | 1.25 | 99.01 | 98.93 | 98.99 | 98.91 | 98.97 | 98.98 | 99.07 | 99.01 | 98.96 | 98.94 |
|  | 0.625 | 98.83 | 98.7 | 98.74 | 98.91 | 98.93 | 98.96 | 98.91 | 98.92 | 98.84 | 98.87 |
|  | 0.313 | 98.71 | 98.73 | 98.72 | 98.91 | 98.76 | 98.78 | 98.69 | 98.73 | 98.65 | 98.84 |
|  | 0.16 | 95.65 | 96.68 | 97.41 | 97.55 | 97.44 | 97.51 | 97.66 | 97.94 | 97.64 | 98.3 |
|  | 0.08 | 29.23 | 47.08 | 71.08 | 78.19 | 60.86 | 70.83 | 62.05 | 79.74 | 80.45 | 91.19 |
|  | 0 | 0 | 12.52 | 15.2 | 5.83 | 26.23 | 20.43 | 31.66 | 30.86 | 40.65 | 50.13 |

TABLE 5

|  |  | ddI (ng/ml) | | | | | | | | | |
|---|---|---|---|---|---|---|---|---|---|---|---|
|  |  | 0 | 2 | 4 | 8 | 16 | 31.25 | 62.5 | 125 | 250 | 500 |
| CDIMI (ng/ml) | 5 | 0 | −0.08 | −0.16 | 0.04 | −0.14 | −0.05 | −0.15 | −0.24 | −0.31 | −0.36 |
|  | 2.5 | 0 | −0.22 | −0.25 | −0.2 | −0.24 | −0.26 | −0.35 | −0.42 | −0.52 | −0.66 |
|  | 1.25 | 0 | −0.2 | −0.17 | −0.16 | −0.3 | −0.23 | −0.25 | −0.31 | −0.45 | −0.57 |
|  | 0.625 | 0 | −0.28 | −0.27 | 0.01 | −0.21 | −0.11 | −0.29 | −0.27 | −0.47 | −0.55 |
|  | 0.313 | 0 | −0.14 | −0.19 | 0.02 | −0.29 | −0.19 | −0.43 | −0.38 | −0.58 | −0.52 |
|  | 0.16 | 0 | 0.49 | 1.1 | 1.65 | 0.65 | 0.97 | 0.63 | 0.95 | 0.22 | 0.47 |
|  | 0.08 | 0 | 8.99 | 31.09 | 44.83 | 13.07 | 27.14 | 10.41 | 28.67 | 22.45 | 26.48 |
|  | 0 | 0 | 0 | 0 | 0 | 0 | 0 | 0 | 0 | 0 | 0 |

TABLE 6

|  |  | ddI (ng/ml) | | | | | | | | | |
|---|---|---|---|---|---|---|---|---|---|---|---|
|  |  | 0 | 2 | 4 | 8 | 16 | 31.25 | 62.5 | 125 | 250 | 500 |
| CDIMI (ng/ml) | 5 | 0 | 0 | −0.109 | 0 | −0.11 | 0 | 0 | −0.163 | −0.027 | −0.206 |
|  | 2.5 | 0 | 0 | 0 | 0 | −0.009 | −0.234 | −0.247 | −0.24 | −0.314 | −0.583 |
|  | 1.25 | 0 | −0.071 | 0 | −0.006 | 0 | −0.101 | 0 | −0.13 | −0.373 | −0.185 |
|  | 0.625 | 0 | 0 | −0.064 | 0 | 0 | 0 | 0 | −0.219 | −0.033 | −0.216 |
|  | 0.313 | 0 | 0 | −0.139 | 0 | −0.007 | −0.061 | 0 | −0.02 | −0.066 | −0.314 |
|  | 0.16 | 0 | 0.2844 | 0.9715 | 0.4164 | 0.4701 | 0.5331 | 0.1417 | 0.7958 | 0 | 0 |
|  | 0.08 | 0 | 3.7472 | 27.209 | 40.615 | 6.1053 | 18.505 | 0 | 22.631 | 17.284 | 23.499 |
|  | 0 | 0 | 0 | 0 | 0 | 0 | 0 | 0 | 0 | 0 | 0 |

TABLE 7

|  |  | ddC (ng/ml) | | | | | | | | | |
|---|---|---|---|---|---|---|---|---|---|---|---|
|  |  | 0 | 2 | 4 | 8 | 16 | 31.25 | 62.5 | 125 | 250 | 500 |
| CDIMI (ng/ml) | 5 | 99.1 | 99.04 | 99.17 | 99.06 | 99.3 | 99.15 | 99.16 | 99.14 | 99.08 | 99.12 |
|  | 2.5 | 98.97 | 99 | 98.95 | 98.93 | 99.04 | 99.02 | 99.09 | 99.05 | 98.92 | 98.87 |
|  | 1.25 | 98.88 | 98.96 | 98.96 | 98.99 | 98.93 | 98.9 | 99.03 | 98.88 | 98.86 | 98.96 |
|  | 0.625 | 98.82 | 98.81 | 98.81 | 98.88 | 98.78 | 98.91 | 98.87 | 98.76 | 98.79 | 98.85 |
|  | 0.313 | 98.61 | 98.68 | 98.66 | 98.68 | 98.87 | 98.88 | 98.66 | 98.76 | 98.65 | 98.84 |
|  | 0.16 | 95.41 | 96.36 | 97.41 | 97.94 | 97.91 | 96.57 | 98.7 | 98.7 | 98.7 | 98.67 |
|  | 0.08 | 1.88 | 69.08 | 72.58 | 89.42 | 90.05 | 97.36 | 98.29 | 98.59 | 98.61 | 98.68 |
|  | 0 | 0 | 6.21 | 14.36 | 14.92 | 18.61 | 42.96 | 62.66 | 83.25 | 98.23 | 98.66 |

TABLE 8

| | | ddC (ng/ml) | | | | | | | | | |
|---|---|---|---|---|---|---|---|---|---|---|---|
| | | 0 | 2 | 4 | 8 | 16 | 31.25 | 62.5 | 125 | 250 | 500 |
| CDIMI (ng/ml) | 5 | 0 | −0.12 | −0.06 | −0.17 | 0.03 | −0.34 | −0.5 | −0.71 | −0.9 | −0.87 |
| | 2.5 | 0 | −0.03 | −0.17 | −0.19 | −0.12 | −0.39 | −0.53 | −0.78 | −1.06 | −1.12 |
| | 1.25 | 0 | 0.01 | −0.08 | −0.06 | −0.16 | −0.46 | −0.55 | −0.93 | −1.12 | −1.02 |
| | 0.625 | 0 | −0.08 | −0.18 | −0.12 | −0.26 | −0.42 | −0.69 | −1.04 | −1.19 | −1.13 |
| | 0.313 | 0 | −0.02 | −0.15 | −0.14 | 0 | −0.33 | −0.82 | −1.01 | −1.33 | −1.14 |
| | 0.16 | 0 | 0.66 | 1.34 | 1.85 | 1.65 | 1.19 | 0.41 | −0.53 | −1.22 | −1.27 |
| | 0.08 | 0 | 61.11 | 56.61 | 72.9 | 69.91 | 53.33 | 34.93 | 15.03 | 0.35 | −0.01 |
| | 0 | 0 | 0 | 0 | 0 | 0 | 0 | 0 | 0 | 0 | 0 |

TABLE 9

| | | ddC (ng/ml) | | | | | | | | | |
|---|---|---|---|---|---|---|---|---|---|---|---|
| | | 0 | 2 | 4 | 8 | 16 | 37.25 | 62.5 | 125 | 250 | 500 |
| CDIMI (ng/ml) | 5 | 0 | 0 | 0 | −0.041 | 0 | −0.006 | −0.269 | −0.607 | −0.823 | −0.664 |
| | 2.5 | 0 | 0 | −0.119 | 0 | 0 | −0.133 | −0.479 | −0.369 | −0.906 | −0.786 |
| | 1.25 | 0 | 0 | 0 | 0 | 0 | −0.383 | −0.165 | −0.802 | −0.452 | −0.892 |
| | 0.25 | 0. | 0 | −0.026 | −0.069 | 0 | −0.112 | −0.613 | −0.809 | −0.727 | −1.079 |
| | 0.313 | 0 | 0 | 0 | 0 | 0 | 0 | −0.023 | −0.702 | −0.996 | −0.832 |
| | 0.16 | 0 | 0.403 | 0 | 1.7472 | 1.5729 | 0.933 | 0 | −0.273 | −1.143 | −1.244 |
| | 0.08 | 0 | 47.618 | 44.582 | 72.566 | 68.856 | 53.253 | 34.493 | 14.85 | 0.0673 | 0 |
| | 0 | 0 | 0 | 0 | 0 | 0 | 0 | 0 | 0 | 0 | 0 |

TABLE 10

| | | saquinavir (ng/ml) | | | | | | | | | |
|---|---|---|---|---|---|---|---|---|---|---|---|
| | | 0 | 2 | 4 | 8 | 16 | 31.25 | 62.5 | 125 | 250 | 500 |
| CDIMI (ng/ml) | 5 | 99.25 | 99.21 | 99.2 | 99.2 | 99.1 | 99.12 | 99.17 | 99.04 | 99.06 | 99.05 |
| | 2.5 | 99.14 | 99.01 | 99.06 | 99.07 | 98.98 | 98.93 | 99.2 | 98.8 | 98.88 | 98.95 |
| | 1.25 | 99.04 | 98.85 | 98.73 | 98.91 | 98.76 | 98.58 | 98.91 | 98.85 | 98.72 | 98.79 |
| | 0.625 | 98.77 | 98.78 | 98.6 | 98.61 | 98.71 | 98.7 | 98.63 | 98.63 | 98.55 | 98.71 |
| | 0.313 | 98.71 | 98.37 | 98.56 | 98.67 | 98.8 | 98.72 | 98.58 | 98.69 | 98.54 | 98.56 |
| | 0.16 | 96.94 | 98.01 | 98.2 | 98.54 | 98.59 | 98.6 | 98.85 | 98.75 | 98.41 | 98.41 |
| | 0.08 | −1.13 | 91.93 | 97.16 | 97.77 | 97.62 | 98.54 | 98.49 | 98.43 | 98.44 | 98.45 |
| | 0 | 0 | 0.91 | −2.49 | 21.48 | 72 | 86.33 | 91.51 | 93.49 | 94.2 | 93.95 |

TABLE 11

| | saquinavir (ng/ml) | | | | | | | | | |
|---|---|---|---|---|---|---|---|---|---|---|
| | 0 | 2 | 4 | 8 | 16 | 31.25 | 62.5 | 125 | 250 | 500 |
| CDIMI (ng/ml) | | | | | | | | | | |
| 5 | 0 | −0.05 | −0.03 | −0.21 | −0.69 | −0.78 | −0.77 | −0.91 | −0.9 | −0.9 |
| 2.5 | 0 | −0.14 | −0.06 | −0.25 | −0.78 | −0.95 | −0.73 | −1.14 | −1.07 | −1 |
| 1.25 | 0 | −0.2 | −0.29 | −0.34 | −0.97 | −1.29 | −1.01 | −1.09 | −1.22 | −1.15 |
| 0.625 | 0 | 0 | −0.14 | −0.42 | −0.95 | −1.13 | −1.27 | −1.29 | −1.38 | −1.22 |
| 0.313 | 0 | −0.35 | −0.12 | 0.32 | −0.84 | −1.1 | −1.31 | −1.23 | −1.39 | −1.36 |
| 0.16 | 0 | 1.04 | 1.34 | 0.94 | −0.55 | −0.98 | −0.89 | −1.05 | −1.41 | −1.4 |
| 0.08 | 0 | 92.14 | 100.81 | 77.18 | 25.94 | 12.36 | 7.08 | 5.01 | 4.31 | 4.57 |
| 0 | 0 | 0 | 0 | 0 | 0 | 0 | 0 | 0 | 0 | 0 |

TABLE 12

| CDIMI (ng/ml) | saquinavir (ng/ml) | | | | | | | | | |
|---|---|---|---|---|---|---|---|---|---|---|
| | 0 | 2 | 4 | 8 | 16 | 31.25 | 62.5 | 125 | 250 | 500 |
| 5 | 0 | 0 | 0 | 0 | −0.484 | −0.574 | −0.641 | −0.833 | −0.592 | −0.515 |
| 2.5 | 0 | 0 | 0 | −0.019 | −0.549 | −0.693 | −0.447 | −0.78 | −0.942 | −0.769 |
| 1.25 | 0 | −0.02 | −0.059 | 0 | −0.739 | −1.084 | −0.599 | −0.807 | −1.066 | −0.996 |
| 0.625 | 0 | 0 | 0 | 0 | −0.822 | −0.899 | −0.833 | −0.802 | −1.174 | −1.117 |
| 0.313 | 0 | 0 | 0 | −0.063 | −0.66 | −0.689 | −0.925 | −0.87 | −1.056 | −0.975 |
| 0.16 | 0 | 0.3461 | 0.3634 | 0.5031 | −0.165 | 0 | −0.376 | −0.793 | −1.307 | −0.629 |
| 0.08 | 0 | 83.531 | 97.957 | 76.049 | 25.349 | 10.664 | 6.566 | 4.5474 | 4.1815 | 4.1588 |
| 0 | 0 | 0 | 0 | 0 | 0 | 0 | 0 | 0 | 0 | 0 |

TABLE 13

| CDIMI (ng/ml) | foscarnet (ng/ml) | | | | | | | | | |
|---|---|---|---|---|---|---|---|---|---|---|
| | 0 | 2 | 4 | 8 | 16 | 31.25 | 62.5 | 125 | 250 | 500 |
| 10 | 98.62 | 98.78 | 98.73 | 98.51 | 98.56 | 98.71 | 98.49 | 98.5 | 98.62 | 98.52 |
| 5 | 98.33 | 98.96 | 98.99 | 99 | 99.02 | 98.77 | 98.74 | 98.66 | 98.73 | 98.85 |
| 2.5 | 97.99 | 98.62 | 98.8 | 99.15 | 98.26 | 98.44 | 98.8 | 98.39 | 98.6 | 98.64 |
| 1.25 | 91.78 | 92.23 | 92.96 | 92.48 | 92.63 | 95.15 | 95.13 | 96.36 | 97.68 | 98.52 |
| 0.625 | 34.93 | 47.31 | 61.09 | 72.46 | 75.1 | 84.61 | 91.03 | 92.57 | 96.28 | 96.98 |
| 0.313 | 33.97 | 39.29 | 47.9 | 53.56 | 63.68 | 72.23 | 87.93 | 90.56 | 93.45 | 96.91 |
| 0.157 | 19.14 | 21.57 | 30.44 | 20.42 | 36.34 | 41.02 | 34.76 | 83.9 | 88.94 | 89.91 |
| 0 | 0 | 15.84 | 11.05 | 25.35 | 33.03 | 32.6 | 40.2 | 54.76 | 75.76 | 83.89 |

TABLE 14

| CDIMI (ng/ml) | foscarnet (ng/ml) | | | | | | | | | |
|---|---|---|---|---|---|---|---|---|---|---|
| | 0 | 2 | 4 | 8 | 16 | 31.25 | 62.5 | 125 | 250 | 500 |
| 10 | 0 | −0.06 | −0.04 | −0.46 | −0.52 | −0.36 | −0.68 | −0.88 | −1.05 | −1.26 |
| 5 | 0 | 0.37 | 0.48 | 0.25 | 0.14 | −0.1 | −0.26 | −0.58 | −0.87 | −0.88 |
| 2.5 | 0 | 0.31 | 0.59 | 0.65 | −0.39 | −0.21 | 0 | −0.7 | −0.91 | −1.04 |
| 1.25 | 0 | −0.85 | 0.27 | −1.38 | −1.87 | 0.69 | 0.05 | 0.08 | −0.33 | −0.16 |
| 0.625 | 0 | 2.07 | 18.97 | 21.03 | 18.68 | 28.47 | 29.94 | 22.01 | 12.05 | 7.46 |
| 0.313 | 0 | −5.14 | 6.63 | 2.85 | 7.9 | 16.73 | 27.42 | 20.43 | 9.46 | 7.55 |
| 0.157 | 0 | −10.38 | 2.36 | −19.22 | −9.51 | −4.48 | −16.89 | 20.48 | 8.54 | 2.94 |
| 0 | 0 | 0 | 0 | 0 | 0 | 0 | 0 | 0 | 0 | 0 |

TABLE 15

| CDIMI (ng/ml) | foscarnet (ng/ml) | | | | | | | | | |
|---|---|---|---|---|---|---|---|---|---|---|
| | 0 | 2 | 4 | 8 | 16 | 31.25 | 62.5 | 125 | 250 | 500 |
| 10 | 0 | 0 | 0 | 0 | 0 | 0 | 0 | 0 | 0 | −0.566 |
| 5 | 0 | 0 | 0.0945 | 0 | 0 | 0 | 0 | 0 | 0 | 0 |
| 2.5 | 0 | 0 | 0 | 0 | 0 | 0 | 0 | 0 | 0 | −0.86 |
| 1.25 | 0 | 0 | 0 | 0 | 0 | 0 | 0 | 0 | 0 | 0 |
| 0.625 | 0 | 0 | 0 | 0 | 0 | 0 | 16.242 | 14.917 | 7.5525 | 2.9368 |
| 0.313 | 0 | 0 | 0 | 0 | 0 | 0 | 19.53 | 8.4024 | 0 | 4.9029 |

TABLE 15-continued

| | foscarnet (ng/ml) | | | | | | | | |
|---|---|---|---|---|---|---|---|---|---|
| | 0 | 2 | 4 | 8 | 16 | 31.25 | 62.5 | 125 | 250 | 500 |
| 0.157 | 0 | 0 | 0 | 0 | 0 | 0 | 0 | 0.0742 | 1.1641 | 0 |
| 0 | 0 | 0 | 0 | 0 | 0 | 0 | 0 | 0 | 0 | 0 |

All data analyses were conducted by Mac Synergy II soft (Prichard, M. N. and Shipman, C., Jr., Antiviral Res 14: 181–206, 1990). According to the manual, synergy volume was judged as follows; when synergy volume is 25–50, the synergy is small but significant (+), when synergy volume is 50–100, the synergy is significant (++), and when synergy volume is more than 100, the synergy is very high (+++).

Synergy volume within 99% confidential limit and the results of judgment are shown in Table 16.

TABLE 16

| Anti-HIV compound | Synergy volume | Synergy |
|---|---|---|
| CDIMI + AZT | 405 | +++ |
| CDIMI + ddI | 163 | +++ |
| CDIMI + ddC | 341 | +++ |
| CDIMI + saquinavir | 314 | +++ |
| CDIMI + foscarnet | 76 | ++ |

Table 16 shows very high synergy of CDIMI in the combination with other anti-HIV compounds.

Experiment 2
Cytotoxicity and Cell Growth Inhibition

For a cytotoxicity test and a cell growth inhibition test, 96-well flat bottom microplates were used. CDIMI from 50 µg/ml to 0.78 µg/ml in two-fold dilution and 0 µg/ml, and AZT from 200 µg/ml to 0.18 µg/ml in two-fold dilution and 0 µg/ml were prepared and two drugs were combined by the checker board method.

(Cytotoxicity test)

Figure 2:
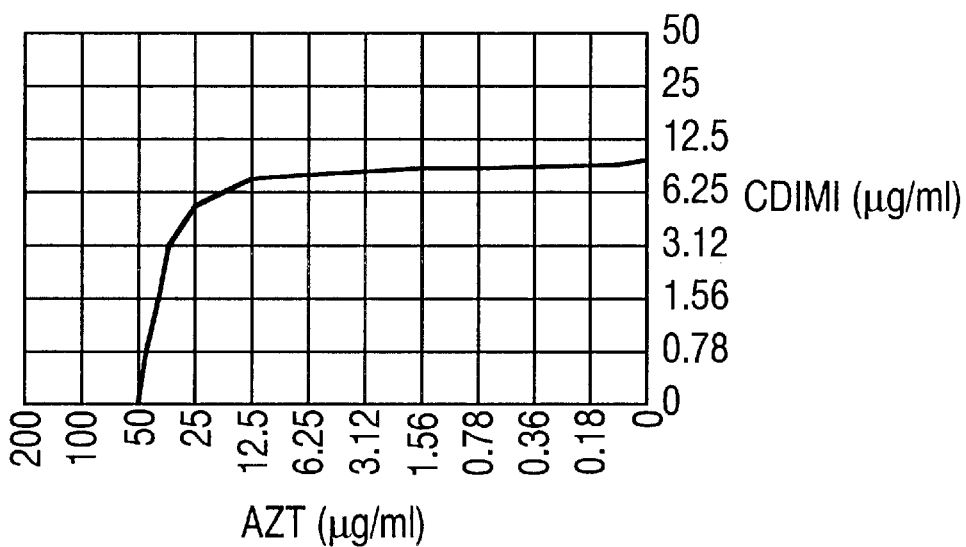
FIG. 2 shows correlation between a concentration of an anti-HIV compound and a toxicity ($CC_{50}$) to U937 cells.

CEM cells or U937 cells were cultured in RPMI-1640 medium supplemented with 10% fetal calf serum. The cells were added to each well of 96 well flat bottom microplates at $1 \times 10^4$ cells per well, and CDIMI and AZT diluted in the same medium were added to each well according to the above method. The plates were incubated in 5% $CO_2$ incubator at 37° C. for 3 days, and to all wells were added 5 mg/ml of MTT (3{4,5-dimethylthiazol-2-yl}-2,5-diphenyltetrazolium bromide) and 30 µl of PBS and incubated for 1 hour. During this incubation, surviving cells reduced MTT to insoluble formazan. From all wells 150 µl of the culture supernatant was taken out and then 150 µl of a solution (isopropanol containing 10% Triton X-100 and 0.4% HCl) was added. Formazan was solubilized by shaking and $OD_{560}$ nm was measured using $OD_{690}$ nm as reference wavelength. Fifty % cytotoxic concentration ($CC_{50}$) was calculated and plotted results are shown in FIG. 1 and FIG. 2. FIG. 1 is the result using CEM cells and FIG. 2 is the result using U937 cells.

(Cell growth inhibition test)

Figure 3:
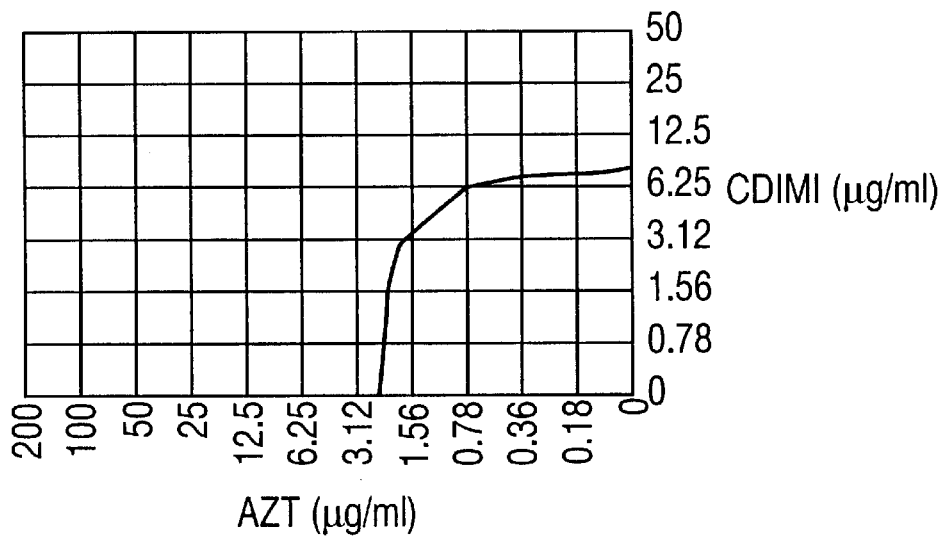
FIG. 3 shows correlation between a concentration of an anti-HIV compound and a growth inhibition ($IC_{50}$) to CEM cells.
Figure 4:
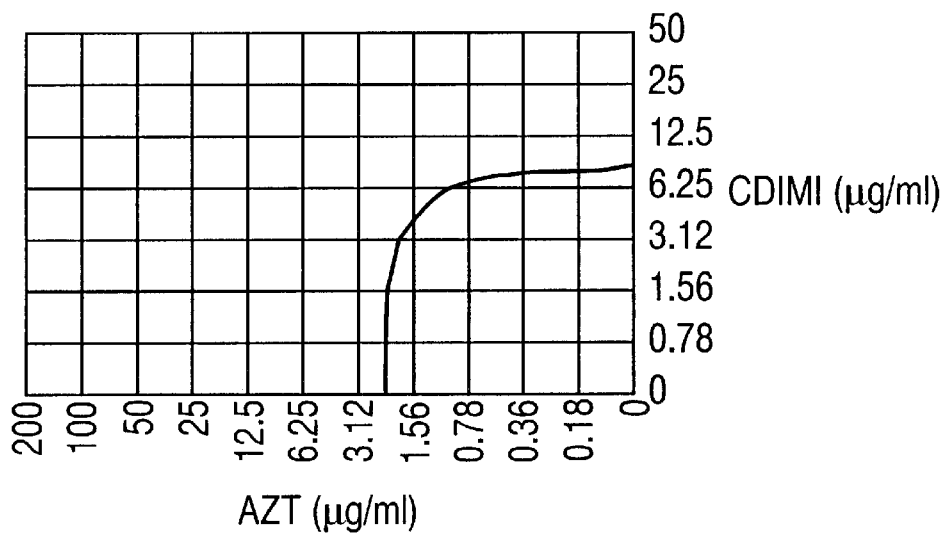
FIG. 4 shows correlation between a concentration of an anti-HIV compound and a growth inhibition ($IC_{50}$) to U937 cells.

CEM cells or U937 cells were cultured in RPMI-1640 medium supplemented with 10% fetal calf serum. The cells were added to each well of 96 well flat bottom microplates at $1 \times 10^4$ cells per well, and CDIMI and AZT diluted in the same medium were added to each well by the above method. The plates were incubated in 5% $CO_2$ incubator at 37° C. for 5 hours, and to each well was added 0.2 µCi [$^3$H] thymidine and incubated for 24 hours. The cells were collected by a cell harvester on a DEAE filter. Radioactivity incorporated in the cells was measured by Beta Plate scintillation counter to determine cell growth. Fifty % inhibition concentration of [$^3$H] thymidine uptake ($IC_{50}$) was calculated and plotted results are shown in FIGS. 3 and FIG. 4. FIG. 3 is the result using CEM cells and FIG. 4 is the result using U937 cells.

FIG. 1 to FIG. 4 show that combination of CDIMI with AZT does not have synergy in both cytotoxity and cell growth inhibition.

Experiment 3
Suppression of the Emergence of Drug Resistant Variants an T cell line Molt-4 cells persistently infected with HIV-1 (IIIB strain clone 3) were cultured in RPMI-1640 medium supplemented with 10% fetal calf serum, the supernatant was filtered and stored at 80° C., after the virus titer was determined.

One ml of the above medium containing $10^6$ cells of M 8166 was added to each well of 12-well plates, and 100 µl of the above HIV-1 IIIB strain clone 3 was added, and incubated for 2 hours for virus infection. Cells were washed with the above medium, and 4 ml of the medium containing CDIMI or other anti-HIV compounds alone or their combination was added to each well and incubated in 5% $CO_2$ incubator at 37° C. CDIMI was added at 1 ng/ml and ddC was added at 50 ng/ml respectively and the same concentrations of them were added for the combination. Cells were subcultured twice a week, and when viral growth was observed, the drug concentration of the anti-HIV compound was doubled. In the case that no viral growth was observed, the drug concentration was kept the same as that of the last culture.

Virus titer was determined using viral reverse transcriptase activity as a marker by the following method.

To 100 µl of the reaction mixture containing 50 mM Tris-HCl, pH 8.3, 150 mM KCl, 10 mM $MgCl_2$, 0.1% Nonidet P-40, 10 mM dithiothreitol, 5 µg/ml poly(A), 5 µg/ml (dT) $_{12\text{-}18}$, and 1 µCi [$^3$H] dTTP was added 10 µl of the culture supernatant, and incubated at 37° C. for 3 hours. The reaction mixture was chilled on ice and collected by a cell harvester on a DEAE-Filtermat. The filter was washed with 5% $Na_2HPO_4 \cdot 12H_2O$ and $H_2O$, and the radioactivity incorporated in DNA was measured by an LKB Beta Plate scintillation counter to determine viral reverse transcriptase activity.

When virus growth was observed, viruses were isolated and the sensitivity to each active ingredient was assayed by the usual method. The result is shown in Table 17.

TABLE 17

| Anti-HIV compound | Week of emergence of resistant mutants | Ratio of resistance compared to parent strain |
|---|---|---|
| CDIMI | 4 weeks | 10 times |
| ddC | 1 week | 20 times |
| CDIMI + ddC | >5 weeks | — |

Table 17 shows that a resistant variant did not appear in the combination of ddC and CDIMI.

Experiment 4
Revision to Drug Sentitive Virus by the Combination of Drug Resistant Mutations By in vitro mutagenesis to cDNA molecular clone NL432 of HIV, various mutant clones of the reverse transcriptase gene known as CDIMI resistant or AZT resistant were prepared. The mutant clones' cDNAs were transfected to SW480 cells. The produced mutant viruses were infected to MT-4 cells in the same method as described in Experiment 1 in the presence of the drug. After 4 days, viral growth was assayed using reverse transcriptase activity as a marker. Fifty % viral growth inhibition ($EC_{50}$) and 90% viral growth inhibition ($EC_{90}$) were calculated. The result is shown in Table 18.

TABLE 18

| | CDIMI | | AZT | |
|---|---|---|---|---|
| Virus | $EC_{50}$ (ng/ml) | $EC_{90}$ (ng/ml) | $EC_{50}$ (ng/ml) | $EC_{90}$ (ng/ml) |
| NL432 (Wild strain) | 0.31 | 1.1 | 1.2 | 5.6 |
| Y181C | 4.2 | 18 | 0.9 | 3.6 |
| F227C | 2.4 | 9.8 | 0.14 | 1.1 |
| L234I | 6.8 | 14 | 0.78 | 3.0 |
| V106A + F227L | 117 | 310 | 0.58 | 6.0 |
| D67N + K70R | 0.31 | 1.0 | 2.0 | 32 |
| T215Y | 0.17 | 0.4 | 5.6 | 37 |
| T215Y + L234I | 0.69 | 2.7 | 1.6 | 6.8 |

Y181C, F227C, L234I and V106A plus F227L strains imparting CDIMI resistance were sensitive to AZT. Conversely, sensitivity of AZT resistant clones D67N plus K70R and T215Y strains to CDIMI was equivalent to that of the wild strain. That is, CDIMI and AZT do not show cross resistance.

T215Y plus L234I strain having both the AZT-resistant mutation T215Y and the CDIMI-resistant mutation L234I was sensitive to CDIMI and AZT at the same level as the wild strain's, indicating the revision of the resistant to the sensitive. This in vitro result shows that the emergence of resistant variants to both CDIMI and AZT will be unlikely in infected patients to whom CDIMI and AZT are administered simultaneously.

Formulation 1 Granules
The granules were prepared by mixing uniformly the following each ingredient, fluid-granulating, dried, and filtered.

| CDIMI | 20 mg |
|---|---|
| AZT | 25 mg |
| Starch | 15 mg |
| Lactose | 16 mg |
| Crystalline cellulose | 21 mg |
| Polyvinyl alcohol | 3 mg |
| Water | 30 mg |
| Total | 130 mg |

Formulation 2 Capsules The capsules were manufactured by mixing uniformly the following each ingredient, and filling the mixture in gelatin capsules.

| CDIMI | 35 mg |
|---|---|
| ddI | 55 mg |
| Lactose | 96 mg |
| Sodium starch glycolate | 13 mg |
| Magnesium stearate | 1 mg |
| Total | 200 mg |

Formulation 3 Tablets
The tablets of 200 mg were prepared by mixing uniformly the following ingredients other than magnesium stearate and granulated, followed by addition of magnesium stearate.

| CDIMI | 7 mg |
|---|---|
| ddC | 10 mg |
| Lactose | 100 mg |
| Crystalline cellulose | 75 mg |
| Talc | 5 mg |
| Carboxymethylcellulose | 2 mg |
| Magnesium stearate | 1 mg |
| Total | 200 mg |

EFFECT OF INVENTION

As shown obviously in the above experiments, an anti-HIV composition of the present invention, as compared with administration of each anti-HIV compound alone, shows potent synergy in activity, and does not show synergy in citotoxicity. Accordingly, the composition is an effective pharmaceutical composition for treating and preventing of AIDS.

What is claimed is:

1. An anti-HIV composition comprising 2-carbamoyloxymethyl-5-(3,5-dichlorophenylthio)-4-isopropyl-1-(pyridin-4-yl)methyl-1H-imidazole or the pharmaceutically acceptable salt thereof and another one or more anti-HIV compounds.

2. The anti-HIV composition as claimed in claim 1, wherein the anti-HIV compounds show synergy in combination with 2-carbamoyloxymethyl-5-(3,5-dichlorophenylthio)-4-isopropyl-1-(pyridin-4-yl)methyl-1H-imidazole or the pharmaceutically acceptable salt thereof, with the proviso that said anti-HIV compounds exclude non-nucleoside reverse transcriptase inhibitors.

3. The anti-HIV composition as claimed in claim 1, wherein the anti-HIV compounds inhibit the emergence of drug resistant HIV viruses in combination with 2-carbamoyloxymethyl-5-(3,5-dichlorophenylthio)-4-isopropyl-1-(pyridin-4-yl)methyl-1H-imidazole or the pharmaceutical acceptable salt thereof.

4. The anti-HIV composition as claimed in claim 1, wherein the anti-HIV compounds are a nucleoside reverse transcriptase inhibitor selected from the group consisting of AZT, ddI, ddC, d4T and 3TC, a non-nucleoside reverse transcriptase inhibitor selected from the group consisting of 3-(5-(3,5-dichlophenvlthio)-4-isopropyl-1-(pyridin-4-ylmethyl-1H-imidazol-2-ylpropan-1-ol and 2-(5-(3,5-dichlorophenylthio)-1-ethyl-4-isopropyl-1H-imidazol-2-yl) ethanol, and/or an HIV protease inhibitor selected from the group consisting of saquinavir, indinavir, ritonavir, nelfinavir and VX-478.

5. The anti-HIV composition as claimed in claim 1 or 2, wherein the anti-HIV compounds are AZT (azidothymidine) ddI (2',3-dideoxyinosine), ddC (2,3'-dideoxycytidine),3TC (3-thiacytidine),saquinavir, and/or foscarnet.

6. A method for treating AIDS which comprises simultaneously or continuously administering 2-carbamoyloxymethyl-5-(3,5-dichlorophenylthio)-4-isopropyl-1-(pyridin-4-yl)methyl-1H-imidazole or the pharmaceutically acceptable salt thereof and another one or more anti-HIV compounds.

7. The anti-HIV composition as claimed in claim 2, wherein the anti-HIV compounds are AZT (azidothymidine), ddI(2',3-dideoxyinosine),ddC(2,3'-dideoxycytidine),3TC(3'-thiacytidine), saquinavir, and/or foscarnet.

8. A method for treating AIDS which comprises simultaneously or continuously administering 2-carbamoyloxymethyl-5-(3,5-dichlorophenylthio)-4-isopropyl-1-(pyridin-4-yl)methyl-1H-imidazole or the pharmaceutically acceptable salt thereof and another one or more anti-HIV compounds.

* * * * *